(12) United States Patent
Novak

(10) Patent No.: US 6,997,896 B2
(45) Date of Patent: *Feb. 14, 2006

(54) APPARATUS FOR IRRIGATING A BODY CAVITY WITH A LIQUID

(75) Inventor: Pavel Novak, Stetten (CH)

(73) Assignee: Karl Storz GmbH & Co. KG (DE)

( * ) Notice: Subject to any disclaimer, the term of this patent is extended or adjusted under 35 U.S.C. 154(b) by 200 days.

This patent is subject to a terminal disclaimer.

(21) Appl. No.: 10/386,015

(22) Filed: Mar. 11, 2003

(65) Prior Publication Data

US 2003/0236488 A1 Dec. 25, 2003

Related U.S. Application Data

(63) Continuation-in-part of application No. 10/323,247, filed on Dec. 19, 2002.

(30) Foreign Application Priority Data

Jun. 24, 2002 (EP) .............................. 02014113

(51) Int. Cl.
A61M 31/00 (2006.01)

(52) U.S. Cl. ......................................... 604/67; 606/107
(58) Field of Classification Search .................. 604/67, 604/27–28, 30–31, 43, 65; 606/107; 607/62
See application file for complete search history.

(56) References Cited

U.S. PATENT DOCUMENTS

| | | | |
|---|---|---|---|
| 3,930,505 A | * | 1/1976 | Wallach ....................... 604/22 |
| 4,261,360 A | | 4/1981 | Perez |
| 4,650,462 A | | 3/1987 | DeSatnick et al. |
| 4,902,277 A | | 2/1990 | Mathies et al. |
| 5,000,733 A | | 3/1991 | Mathies et al. |
| 5,131,823 A | | 7/1992 | Guignard |
| 5,556,378 A | * | 9/1996 | Storz et al. ................... 604/31 |
| 5,685,821 A | | 11/1997 | Pike |
| 6,579,255 B1 | * | 6/2003 | Kadziauskas et al. ......... 604/35 |

FOREIGN PATENT DOCUMENTS

| | | |
|---|---|---|
| DE | 4219890 A1 | 1/1994 |
| EP | 0529902 A2 | 8/1991 |
| EP | 02014113 | 2/2003 |
| WO | WO 00/78372 A1 | 6/2000 |

* cited by examiner

Primary Examiner—Nicholas D. Lucchesi
Assistant Examiner—Catherine S. Williams
(74) Attorney, Agent, or Firm—St. Onge Steward Johnston & Reens LLC

(57) ABSTRACT

An apparatus for controlling the pressure of a liquid, introduced into a body cavity, in order to facilitate a surgical procedure, utilizing an irrigation pump and conduit and at least one output device and conduit leading away from the body cavity for drawing off the liquid, and a control circuit for controlling the irrigation pump and output device such that a nominal pressure in the cavity may be maintained.

34 Claims, 7 Drawing Sheets

APPARATUS FOR IRRIGATING A BODY CAVITY WITH A LIQUID

PRIORITY DOCUMENT

The present application is a continuation-in-part of U.S. patent application Ser. No. 10/323,247 filed Dec. 19, 2002.

FIELD OF THE INVENTION

The invention relates to an apparatus for automatically controlling the introduction and removal of a fluid into a body cavity in order to facilitate a surgical procedure, where the pressure and the flow rate of the fluid in the cavity is automatically controlled so as to ensure to safety of the patient.

BACKGROUND OF THE INVENTION

The apparatus of the present invention is used for the endoscopic irrigation of body cavities, for example the bladder, the uterus or articular capsules.

The apparatus may be specially used in arthroscopy in an endoscopic resection of a joint. In this connection, a physiological liquid is pumped by means of an irrigation pump through an irrigation conduit into the joint. The liquid is then drawn off from the joint by means of a suction pump through a suction conduit.

It is desirable during such an endoscopic irrigation of hollow organs that the pressure and the flow rate of the irrigation liquid in the body cavity can be adjusted independently from one another. The flow rate is to be understood as the liquid volume through the body cavity per time unit.

U.S. Pat. No. 4,902,277 ("the '277 patent") discloses a system for irrigating a body cavity utilizing an irrigation pump with a feed conduit connected to a body cavity for feeding fluid into the body cavity and a suction pump connected to a suction conduit for removing fluid from the body cavity. A pressure transducer controls the irrigation pump while a speed transducer controls the suction pump.

However, a major disadvantage the '277 patent is observed when an obstruction which is, for example, caused by tissue pieces, occurs in the suction conduit. In case of an obstruction in the suction conduit, the actual pressure in the body cavity may exceed the nominal pressure with the result that the irrigation pump of the known apparatus is controlled such that its speed decreases, in order to maintain the nominal pressure. In contrast to that, the suction pump that is adjusted to the predetermined nominal flow rate, works on with an unchanged speed. The result is that the suction pump does not work harder to draw off the obstruction and the irrigation pump eventually shuts down as pressure increases leaving the body cavity pressurized. This can lead to a disturbance and interruption of the irrigation operation and, thereby, of the medical operation. Therefore, it is undesirable to control the suction pump with a speed control or control the irrigation pump with a pressure transducer.

On the other hand, an apparatus for irrigating a body cavity is known from EP 0 529 902 A2, the irrigation pump of which is a centrifugal pump, which is controlled as a function of a predetermined nominal pressure in the body cavity or in the irrigation conduit, respectively, while the suction pump is a displacement pump in form of a gear pump. Unlike a displacement pump, a centrifugal pump has the characteristic that the produced flow rate is not a single-valued function of the speed of the centrifugal pump, but in addition depends on the actual pressure. With this known apparatus, the flow rate is adjusted by means of a controllable tube-squeezing valve.

However, EP 0 529 902 A2 has the disadvantage that the irrigation pump, which is designed as a centrifugal pump, is not sealing so that in case that the squeezing valve is not closed and both pumps are not activated, the liquid can flow through without impediment as a result of the gradient. Another disadvantage of EP 0 529 902 A2 is, as mentioned before, that by using a centrifugal pump as the irrigation pump, the flow rate cannot be preset in exact manner because neither the irrigation pump nor the suction pump allow a simple dependency of the flow rate, for example as a function of the speed of the pumps. In this known apparatus, the actual flow rate highly depends on the pressure difference in the system.

It is an object of the invention to provide an apparatus of the afore-mentioned kind by means of which the pressure and the flow rate can be controlled as independently from each other as possible.

SUMMARY OF THE INVENTION

According to the invention, this object is achieved in that a control circuit controls an irrigation pump as a function of the nominal flow rate, while it controls the suction pump as a function of the nominal pressure.

The suction pump is a displacement pump, which is controlled as a function of the actual pressure in the irrigation conduit or in the body cavity, which is measured by a pressure sensor, in order to maintain a predetermined nominal pressure in the body cavity. The speed of the motor of the suction pump is increased or reduced as a function of the actual pressure measured by the pressure sensor, in order to maintain the nominal pressure in the body cavity.

The irrigation pump is a displacement pump, too, which is controlled as a function of the actual flow rate. In this connection, two flow rates may be adjusted, as a function of which the irrigation pump is controlled. The irrigation pump maintains a selected flow rate, which has been set respectively. The higher nominal flow rate may be set, for example, when a working instrument, for example a resection instrument, is additionally put into operation. The lower flow rate may be set, for example, when the body cavity is just to be irrigated without a working instrument being in operation.

The use of a displacement pump, in particular a roller pump, has the advantage that the flow rate produced by the pump is, to a high degree, proportional to the speed of the displacement pump in particular if the pressure maintained by the suction pump is constant.

Unlike the '277 patent, the irrigation pump of the apparatus according to the present invention is not controlled as a function of the nominal pressure, but the selected flow rate is adjusted through the irrigation pump. On the other hand, the nominal pressure is adjusted by means of the suction pump, i.e. the suction pump is controlled to the predetermined nominal pressure. This is advantageous in that an obstruction in the suction conduit that causes the actual pressure to exceed the nominal pressure, may be drawn off by virtue of an automatically increasing higher suction power of the suction pump.

In contrast to that, the apparatus disclosed in the '277 patent would only respond to obstructions in the irrigation conduit by reducing the speed of the irrigation pump, this however, will not result in the removal of the obstruction. In fact, if a partial obstruction occurred in the system described in the '277 patent, the irrigation pump could simply slow down to match the lower flow rate of the suction pump, which is only attempting to maintain a selected speed, due to the obstruction and simply maintain this lower flow rate indefinitely. Whereas the present invention measures the actual flow rate through the irrigation conduit to maintain an actual flow rate which would cause an increase in pressure and thereby cause the suction pump to work even harder to draw off the obstruction.

In a preferred embodiment, a pressure sensor is associated with the irrigation conduit for determining the actual pressure, and the control circuit controls the suction pump as a function of the actual pressure determined by the pressure sensor for maintaining the nominal pressure.

The advantage herewith is that the nominal pressure can be maintained in a particular exact manner in that the suction power of the suction pump is increased or reduced as a function of the acquired actual pressure in order to maintain the predetermined nominal pressure in the body cavity.

In a further embodiment, the control circuit controls the irrigation pump as a function of the suction power of the suction pump such that the power of the irrigation pump is reduced when the suction power of the suction pump is increased, at least when the suction power of the suction pump exceeds a predetermined threshold value.

This measurement is advantageous in terms of the safety of the apparatus for the patient. In the case of an obstruction causing the actual pressure in the body cavity to exceed a threshold value and causing the suction pump to strongly increase its suction power accordingly, in order to maintain the predetermined nominal pressure, and in case that the obstruction is such that it cannot be removed despite the increasing suction power, the power of the irrigation pump is decreased or even reduced to zero, in order to avoid an excessive pressure in the body cavity and thereby a risk for the patient. Thus, when an obstruction cannot be removed by a high suction rate, irrigation liquid will not continue to be pumped into the body cavity creating a hazard for the patient.

In a further embodiment, the irrigation pump and/or the suction pump are displacement pumps. The use of displacement pumps has the advantage in that control of these pumps may be accomplished simply via the speed, wherein another advantage is that the produced debit or flow rate is a substantially single-valued function of the speed of the pump.

In this connection, it is preferred if the irrigation pump is a roller pump or a gear pump. A roller pump is a displacement pump in which a plurality of rollers is moved along a flexible conduit portion, whereby the liquid conduit is peristaltically narrowed in cross-section. The use of the roller pump is particularly preferred because the flow rate is correlated with the speed of the roller pump in a single-valued manner.

In comparison to that, the use of a gear pump as the irrigation pump has the advantage that the irrigation liquid is fed into the body cavity in a manner substantially free of pulsations.

It is further preferred if the suction pump is a roller pump. Although a roller pump is not suited to produce a flow free of pulsations, which is, however, not absolutely necessary for the irrigation pump, the irrigation pump has a particularly simple construction and it is noted that there is a single-valued correlation between the flow rate and the speed of the pump.

In various alternative embodiments, it may also be preferred if the irrigation pump is a centrifugal pump. In order to advantageously obtain a fixed correlation between the flow rate and the speed, the actual correlation between the flow rate and the speed is first determined for a certain type of a centrifugal pump, and the control circuit then uses the determined correlation for controlling the irrigation pump, in order to adjust or maintain the predetermined flow rate.

In a further embodiment, the control circuit uses the speed of the suction pump as a control signal and controls the irrigation pump as a function of said control signal. This embodiment is advantageous in case a gear pump is used as the irrigation pump, for which the flow rate is not correlated with the speed of the pump in a single-valued manner, as it usually is the case for a roller pump. The flow rate of a gear pump depends on the suction pressure as well as on the irrigation pressure. For this reason, it is not possible to control the flow rate only by means of the speed of the gear pump, but a regulation is required. Such a regulation of the speed of the irrigation pump can be easily obtained in the afore-mentioned manner as a function of the speed of the suction pump that is preferably configured as a roller pump. In addition, this embodiment is also suited for improving the safety of the apparatus for the patient.

In connection with one of the afore-mentioned embodiments according to which the control circuit controls the irrigation pump as a function of the suction power of the suction pump such that upon an increase of the suction power, at least if the latter exceeds a predetermined threshold value, the power of the irrigation pump is reduced, it is provided in a further preferred embodiment that the control circuit controls the irrigation pump as a function of the speed of the suction pump at least when a flow rate threshold value is exceeded such that the speed of the irrigation pump is reduced when the speed of the suction pump increases.

This embodiment also has the advantage of a control of the irrigation pump, which may be realized in a particularly simple manner as a function of the suction power of the suction pump, which results in the desired effect that a danger by an increase of pressure in the body cavity is avoided.

In a further embodiment, the control circuit may also control the irrigation pump as a function of the difference between the speeds of the irrigation pump and the suction pump.

In still another embodiment, the control circuit controls the irrigation pump as a function of at least two different nominal flow rates. With this embodiment, at least two different nominal flow rates may be adjusted through the irrigation pump. In a surgical operation, e.g. an endoscopic operation, the liquid volume through the body cavity may be increased, for example when tissue is dissected in the body cavity so that blood and tissue pieces may be withdrawn in a more efficient manner by virtue of an increased irrigation flow.

In this connection, it is preferred if the control circuit switches over the irrigation pump between the at least two nominal flow rates as a function of the operating condition of a working instrument connected with the control circuit.

The advantage is that the changeover between the at least two nominal flow rates occurs in an automatic manner when the working instrument is switched on or switched off, respectively, so that the physician has not to carry out the changeover herself or himself and is, therefore, not distracted from her or his operative activity.

In a further embodiment, at least two parallel suction conduits lead away from the body cavity, wherein the suction pump is associated with both suction conduits, wherein one suction conduit is connected with a working instrument, and wherein it may be switched over between both suction conduits as a function of the operating condition of the working instrument.

In this case, the working instrument used for a surgical operation, e.g. a resection instrument, is simultaneously configured as a suction instrument, and upon actuating the working instrument, the liquid and dissected tissue is then drawn off via the working instrument, wherein the changeover between both suction conduits again occurs in an automatic manner without the physician having to carry out the changeover from his or her side.

In a further preferred embodiment, the control circuit determines the difference between the speeds of the irrigation pump and the suction pump.

This embodiment is advantageous when roller pumps are used as both the irrigation and the suction pumps so that the correlation between the flow rate and the speed is approximately equal. In this case, the afore-mentioned embodiment has the advantage that the loss of liquid in the body cavity, which may be caused by liquid entering into the blood stream, may be accurately determined by subtraction of the speeds of both pumps.

In one advantageous embodiment, an apparatus is provided for irrigating a body cavity with a liquid, comprising an irrigation pump and an irrigation conduit. The irrigation conduit is connected to the irrigation pump at a first end and connected to a body cavity at a second end, and is used for feeding the liquid into the body cavity. The apparatus further includes a suction pump and a suction conduit. The suction conduit is connected to the suction pump at a first end and connected to the body cavity at a second end, and is used for withdrawing the liquid from the body cavity. Finally, the apparatus includes a control circuit that controls the irrigation pump and the suction pump such that the liquid passes through the body cavity substantially with a predetermined nominal pressure and a predetermined nominal flow rate. The control circuit controls the irrigation pump as a function of the nominal flow rate, and controls the suction pump as a function of the nominal pressure.

In another advantageous embodiment, an apparatus is provided for irrigating a body cavity with a liquid, comprising an irrigation pump and an irrigation conduit. The irrigation conduit is connected to the irrigation pump at a first end and connected to a body cavity at a second end, and is used for feeding the liquid into the body cavity. The apparatus further includes a working tool that is insertable into the body cavity, a suction pump and a first suction conduit. The first suction conduit is connected to the body cavity at a first end and connected to the suction pump at a second end, and is used for withdrawing the liquid from the body cavity at a first range of variable flow rates. The apparatus also includes a second suction conduit that is connected to the working tool at a first end and connected to the suction pump at a second end, and is used for withdrawing the liquid from the body cavity at a second range of variable flow rates. The second range of variable flow rates is higher than the first range of variable flow rates. Finally, the apparatus includes a control circuit, which controls the irrigation pump and the suction pump such that the liquid passes through the body cavity substantially with a predetermined nominal pressure and a predetermined nominal flow rate.

In yet another advantageous embodiment, a method is provided for irrigating a body cavity with a liquid, including the steps of providing an irrigation pump, and connecting an irrigation conduit between the irrigation pump and a body cavity, which is used for feeding the liquid into the body cavity. The method further includes the steps of providing a suction pump, and connecting a suction conduit between the body cavity and the suction pump, which is used for withdrawing the liquid from the body cavity. The method also includes the step of providing a control circuit for controlling the irrigation pump and the suction pump so that the liquid passes through the body cavity substantially with a predetermined nominal pressure and a predetermined nominal flow rate. Finally the method includes the steps of controlling the irrigation pump as a function of the nominal flow rate, and controlling the suction pump as a function of the nominal pressure.

In still another advantageous embodiment, a method is provided for irrigating a body cavity with a liquid, comprising the steps of providing an irrigation pump, and connecting an irrigation conduit between the irrigation pump and a body cavity, which is used for feeding the liquid into the body cavity. The method further includes the steps of providing a working tool that is insertable into the body cavity, providing a suction pump, and connecting a first suction conduit between the body cavity and the suction pump, which is used for withdrawing the liquid from the body cavity at a first range of variable flow rates. The method also includes the step of connecting a second suction conduit between the working tool and the suction pump, which is used for withdrawing the liquid from the body cavity at a second range of variable flow rates. The second range of variable flow rates is higher than the first range of variable flow rates. The method further includes the step of providing a control circuit for controlling the irrigation pump and the suction pump so that the liquid passes through the body cavity substantially with a predetermined nominal pressure and a predetermined nominal flow rate. Finally, the method includes the steps of withdrawing the liquid from the body cavity at a first range of variable flow rates through the first suction conduit when the working tool is not activated, and withdrawing the liquid from the body cavity at a second range of variable flow rates through the second suction conduit when the working tool is activated.

In yet another advantageous embodiment, an apparatus is provided for irrigating a body cavity with a liquid, comprising an irrigation pump that is connected to the body cavity by an irrigation conduit and is provided for irrigating the body cavity with the liquid. The apparatus further comprises a suction pump that is connected to the body cavity by an output conduit and is provided for withdrawing the liquid from the body cavity. Finally, the apparatus also comprises a control circuit that controls the irrigation pump according to a measured flow of liquid in the irrigation conduit and controls the suction pump according to a measured pressure in the body cavity.

It is understood that the features recited above and those yet to be explained below may be used not only in the respective combination indicated, but also in other combinations or in isolation, without leaving the context of the present invention.

BRIEF DESCRIPTION OF THE DRAWINGS

Exemplary embodiments of the invention are shown in the drawings and are explained in more detail in the description, which follows. In the drawings.

DETAILED DESCRIPTION OF THE DRAWINGS

Figure 1:
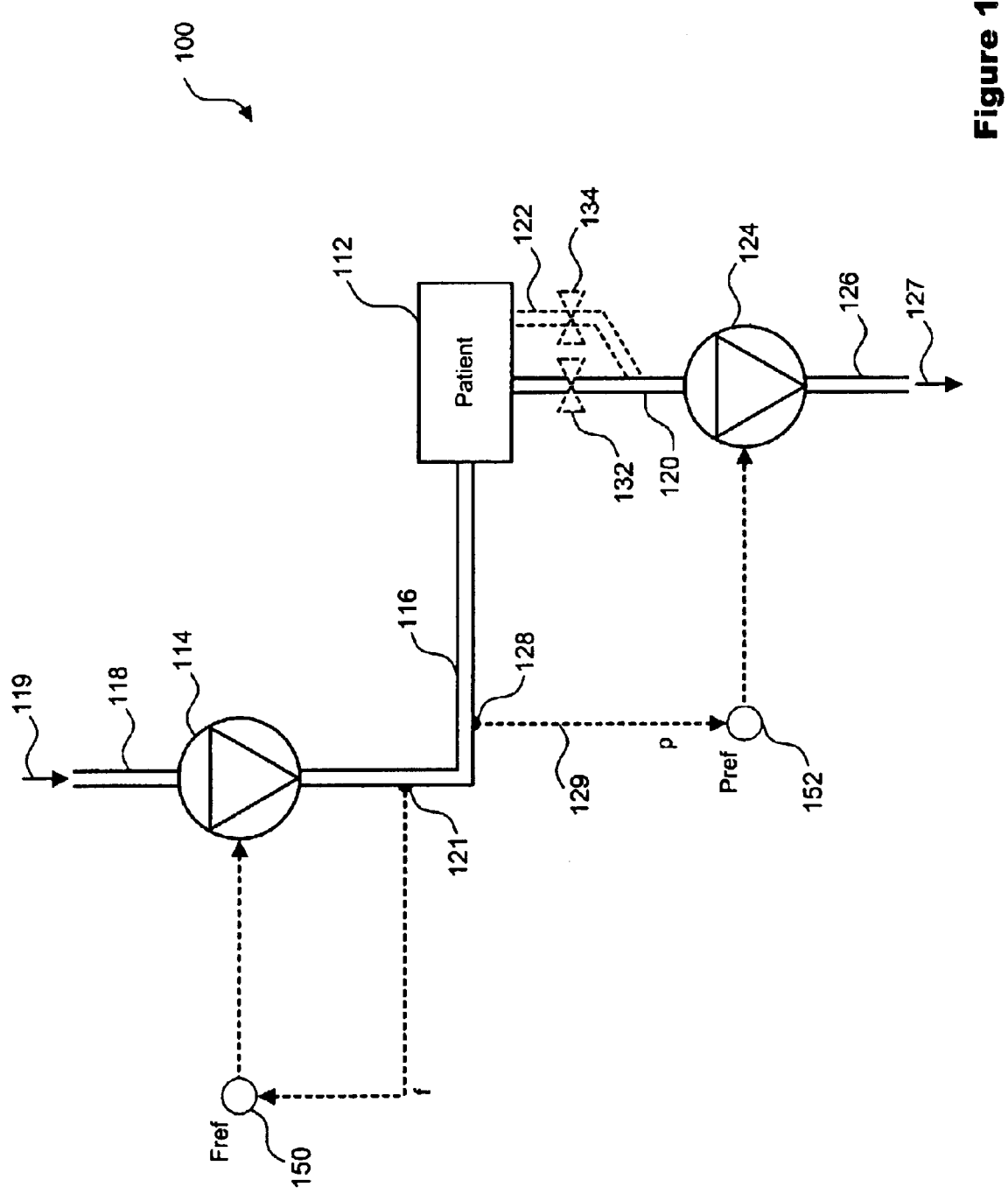
FIG. 1 is a diagram of an apparatus for irrigating a body cavity according to one advantageous embodiment of the present invention.

The apparatus of FIG. 1 is generally labeled with reference numeral 100 for irrigating a body cavity 112 with a liquid. The liquid may be a physiological liquid, for example.

Figure 2:
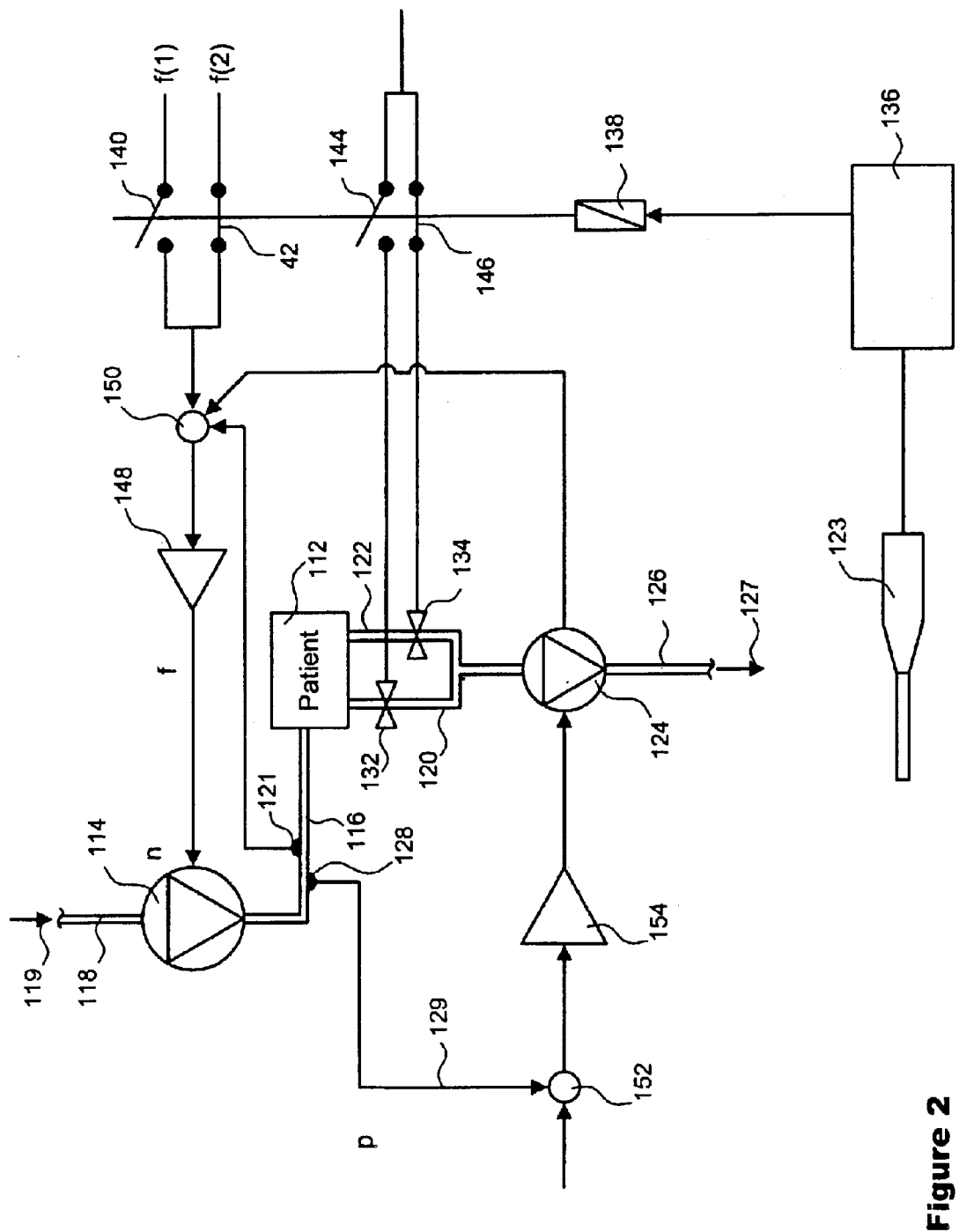
FIG. 2 shows the apparatus in FIG. 1 with further details of the control circuit of the apparatus.

FIG. 2 shows the apparatus 100 together with a schematic representation of a control circuit thereof.

The apparatus 100 is used, for example, for endoscopically irrigating the bladder, the uterus or, when used in arthroscopy, for irrigating a joint, for example the knee.

Referring to FIG. 1 an apparatus 100 includes an irrigation pump 114 connected to the body cavity 112 with irrigation conduit 116. The liquid is drawn from a liquid reservoir through conduit 118 in the direction of arrow 119.

A first suction conduit 120 extends from the body cavity 112 to a suction pump 124 via valve 132. A second suction conduit 122, connected in parallel with the first suction conduit 120, also leads from the body cavity 112 to the suction pump 124 via valve 134. The first suction conduit 120 is connected with an irrigation instrument not shown in detail, which may be inserted in the body cavity 112. The second suction conduit 122 is connected with a working instrument (not shown). When the working instrument (not shown) is activated, valve 134 will open (and valve 132 will close) to withdraw the liquid through the second suction conduit 122. Conversely, when the working instrument (not shown) is not activated, valve 132 will be open (and valve 134 will be closed) such that the liquid is withdrawn from the body cavity 112 through first suction conduit 120. The liquid is then drained off to a sump (not shown) via conduit 126 in the direction of arrow 127.

The pressure sensor 128 is associated with the irrigation conduit 116, which is capable of determining the actual pressure (p) in the irrigation conduit 116 or in the body cavity 112, respectively. Further, a flow transducer 121 is associated with the irrigation conduit 116, which is capable of determining the actual flow (f) of the liquid through the irrigation conduit 116.

An irrigation pump subtractor or comparator 150 is provided with a flow reference ($f_{Ref}$) signal and receives an output from the flow transducer 121. The irrigation pump subtractor or comparator 334 then compares the two signals and controls the irrigation pump 114 accordingly. Preferably, the irrigation pump 114 is controlled within two dynamically variable flow ranges.

A suction pump subtractor or comparator 152 is also provided with a pressure reference ($p_{Ref}$) signal and receives an output from the pressure transducer 128. The suction pump subtractor or comparator 152 then compares the two signals and dynamically controls the suction pump 124 accordingly.

With reference to FIG. 2, the control circuit further comprises a controller 148, which is connected, at the input side, with a subtractor or comparator 150, which is supplied, at the input side, with the signal of the respectively set flow range $f_1$ or $f_2$, and also with the signal of the actual flow rate f of the liquid through the irrigation conduit 116. The controller 148 is connected, at the output side, with the irrigation pump 114, and feeds a signal corresponding to the nominal flow range.

The pressure sensor 128 feeds a signal to another subtractor or comparator 152, which signal corresponds to the actual pressure p acquired by the pressure sensor 128. The subtractor or comparator 152 is further connected, at the input side, with a nominal pressure value generator (not shown) feeding a signal corresponding to the nominal pressure p to the subtractor or comparator 152. The subtractor or comparator 152 is connected, at the output side, with another controller 154, which is connected, at the output side, with the suction pump 124.

In the following, the control of the apparatus 100 is now described in more detail.

The control of the suction pump 124 for maintaining the nominal pressure p in the body cavity 112 as a function of the actual pressure p determined by the pressure sensor 128 (broken lines 129 in FIG. 1) is such that the speed of the suction pump 124 is increased when the actual pressure p exceeds the nominal pressure p, and the speed of the suction pump 124 is reduced accordingly, when the actual pressure p drops under the nominal pressure p.

The irrigation pump 114 is controlled by the actual flow rate f through the irrigation conduit 116. When the liquid flows unimpeded through the body cavity 112 and no liquid enters into the blood stream, i.e. when the flow rate in the irrigation conduit 116 and in the suction conduit 120 or 122 are equal, an independent adjustment of the flow rate and of the pressure is possible without difficulty.

Now, when the nominal flow rate increases from e.g. $f_2$ to $f_1$ as a function of which the irrigation pump 114 is controlled as already mentioned, the controller 148 will increase the speed of the irrigation pump 114, whereby the actual pressure p in the irrigation conduit 116 would increase. This would cause the suction pump 124 to increase its speed in order to reduce the actual pressure p, and this will be continued as long as the flow rate $f_1$ in the suction conduit 120 or 122 is adjusted to the newly predetermined flow rate $f_1$ in the irrigation conduit 116.

On the other hand, if the pressure p is increased, the controller 154 would slow down the speed of the suction pump 124 for the time. This would result in a control deviation for the irrigation pump 114, which, for the time, increases its speed that results in a further increase of the actual pressure, which further in turn, the suction pump 124 tries to compensate for by an increase of the suction power. In this manner, an increase of the pressure p may be obtained without the nominal flow rate f being changed in the end.

When an obstruction, however, occurs in the suction conduit 120 or 122, or the irrigation conduit 116, that would impede the outflow of the liquid from or into the body cavity 112, another mechanism arises that is caused by the fact that the pressure in the body cavity 112 or the irrigation conduit 116 increases when in general the speed of a roller pump is increased without liquid being able to continue to flow in a sufficient quantity. This will result in the pump tube of the roller pump not reaching its complete cross-section in the suction region, i.e. the pump tube partially collapses so that the flow rate does not increase to the same degree or even decreases despite of the increased speed of the suction pump. This in turn effects the irrigation pump 114, which measures of the actual flow rate f for the irrigation pump 114. This results in the desired effect that the pressure in the body cavity 112 is again reduced or not further increased.

In case of an obstruction as described above, the actual pressure p in the body cavity 112 increases, because the irrigation pump 114 further feeds irrigation liquid via the irrigation conduit 116 into the body cavity 112. Since the suction pump 124 is controlled as a function of the pressure p, the increase of pressure p in the body cavity 112 results in a higher suction power of the suction pump 124 which is manifested in a higher speed of the suction pump 124. In case of smaller obstructions, the increase of the suction power of the suction pump 124 is sufficient to draw off the obstruction. In case, however, the removal of the obstruction is not possible, the speed of the suction pump 124 will further increase and exceed a predetermined threshold value. Feedback of the speed of the suction pump 124 to the control circuitry for the irrigation pump 114 will result in decreasing the speed of the irrigation pump 114.

The irrigation pump 114 is controlled as a function of at least two predetermined nominal flow rates $f_1$ and $f_2$. The two predetermined nominal flow rates $f_1$ and $f_2$ may comprise either two specific flow rates or may comprise two differing flow ranges that may or may not overlap. The control circuit comprises a control unit 136 for the working instrument 123, which automatically switches over between these both nominal flow rates $f_1$ and $f_2$ via e.g. a relay 138 and switches 140 and 142 as a function of the operating condition of the already mentioned working instrument 123 connected with the second suction conduit 122. When the working instrument 123, for example a resection instrument, is actuated, the control circuit automatically adjusts the irrigation pump 114 to the higher nominal flow rate $f_1$ and upon switching off the working instrument, the control circuit automatically switches over to the lower nominal flow rate $f_2$.

Figure 3:
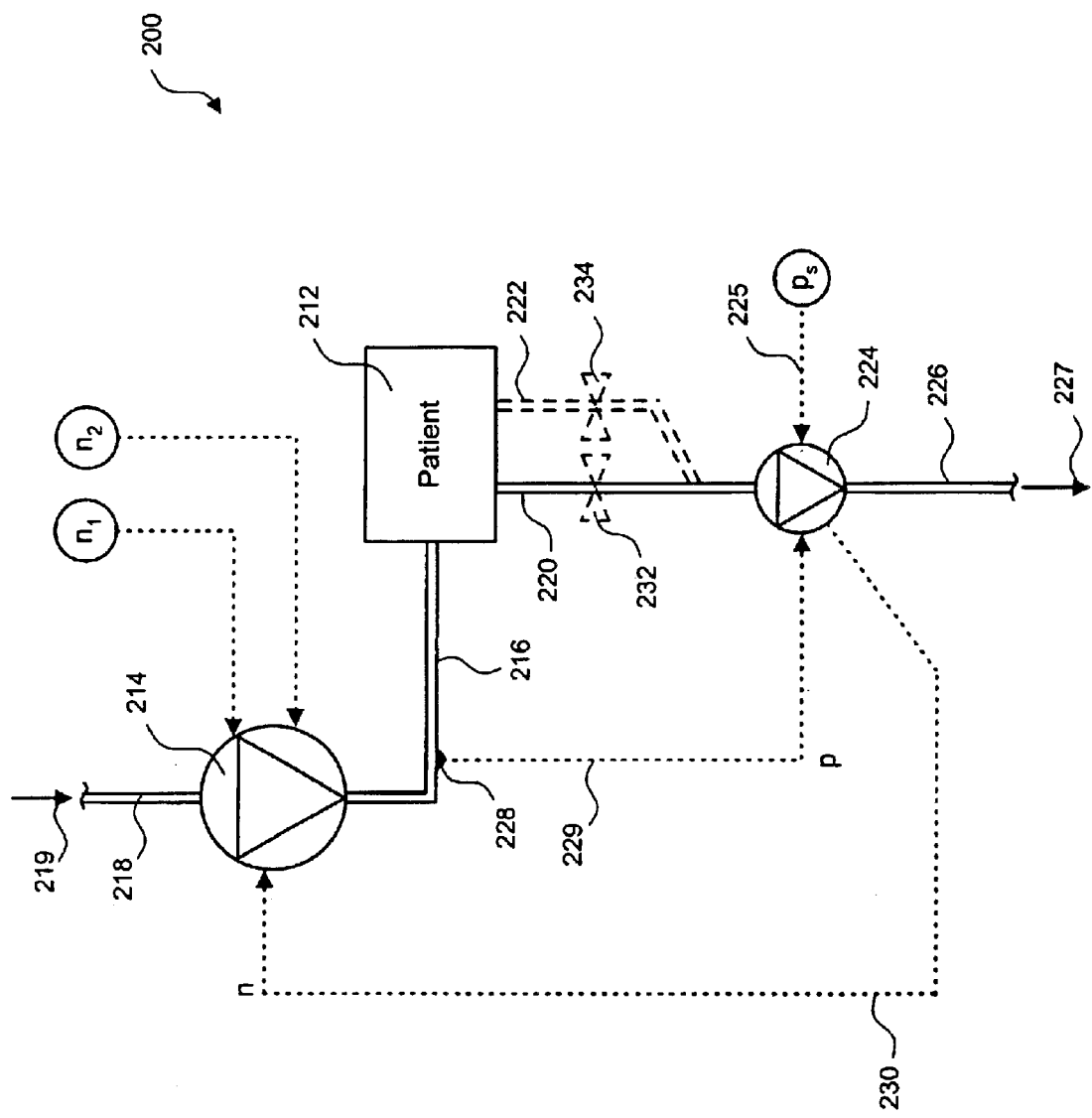
FIG. 3 is a diagram of an apparatus for irrigating a body cavity according to another advantageous embodiment of the present invention.

Referring to FIG. 3, the apparatus 200 comprises an irrigation pump 214 connected with an irrigation conduit 216 leading to the body cavity 212. The liquid is drawn from a liquid reservoir via a conduit 218 according to an arrow 219.

A first suction conduit 220 leads from the body cavity 212 to a suction pump 224 downstream of the body cavity 212. A second section conduit 222, parallel to the first suction conduit 220, also leads from the body cavity 212 to the suction pump 224. The first suction conduit 220 is connected with an irrigation instrument not shown in detail, which may be inserted in the body cavity 212. The second suction conduit 222 is connected with a working instrument 223 schematically shown in FIG. 4, for example a resection instrument, which is used for withdrawing fluid and particles as well as for carrying out an operation in the body cavity 212, for example for removing tissue.

The liquid along with body liquids like blood, secretions and tissue pieces is drawn from the body cavity 212 by means of the suction pump 224 through the first suction conduit 220 or the second suction conduit 222. The liquid drawn off is drained off via a conduit 226 according to an arrow 227 to a collecting vessel (not shown).

The pressure sensor 228 is associated with the irrigation conduit 216, which is capable of determining the actual pressure (p) in the irrigation conduit 216 or in the body cavity 212, respectively. The determination of the actual pressure in the body cavity 212 may be accomplished by calculating the actual pressure in the irrigation conduit 216 if the flow resistance of the irrigation conduit 216 is known.

The irrigation pump 214 is a displacement pump and, in the present instance, the irrigation pump 214 is a roller pump or a gear pump. A roller pump is described, for example, in EP 0 448 909 B1. A roller pump is a peristaltic pump comprising a plurality of rollers arranged on a circular disk rotating about its center axis. When the circular disk rotates, the rollers run along a piece of the tube of the suction conduit 226 and thereby peristaltically change the cross section of this portion of the conduit. A medical gear pump is, for example, described in DE 197 25 462 A1 to the same applicants to which is made reference with respect to an advantageous description of the construction and function of a gear pump.

Figure 4:
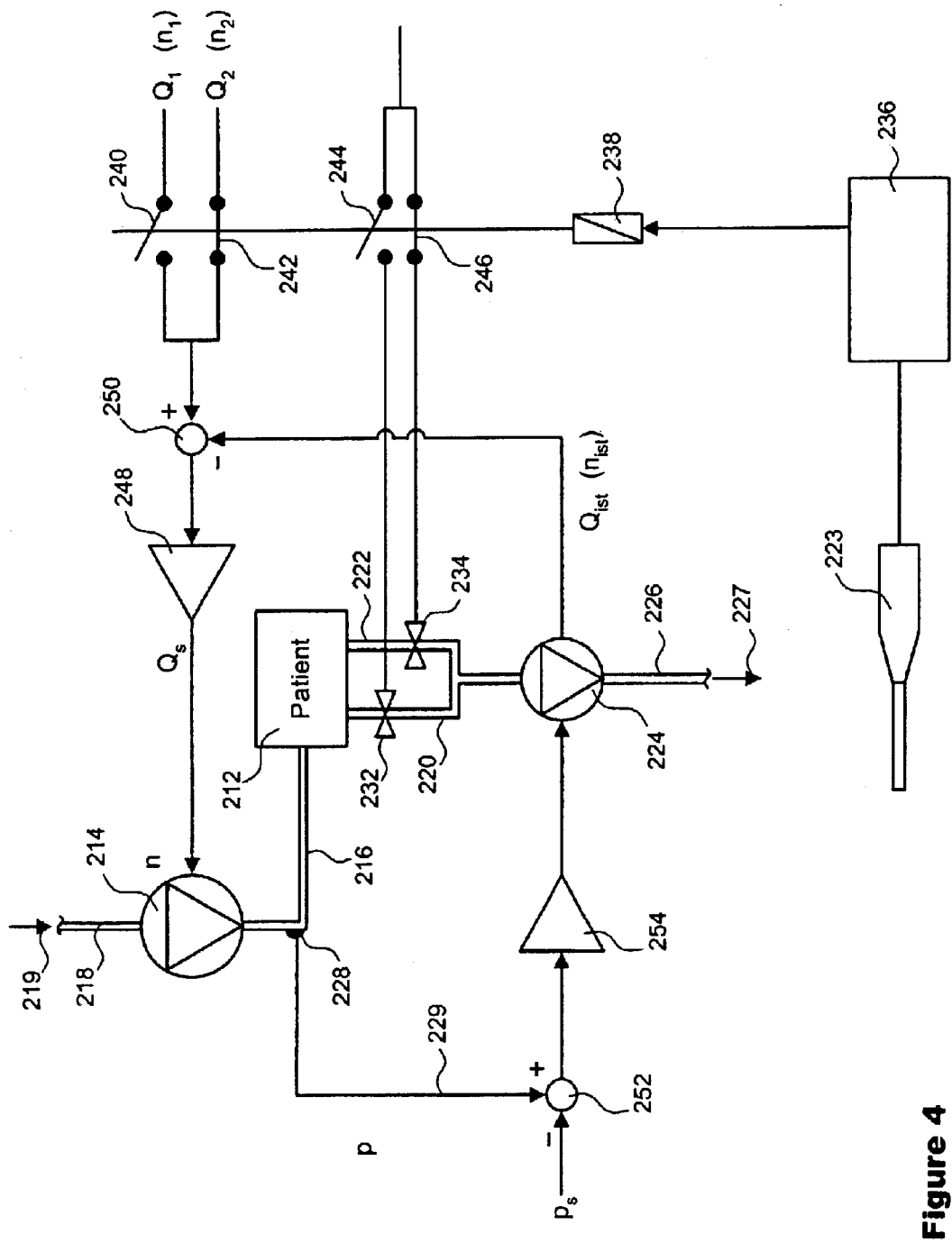
FIG. 4 shows the apparatus in FIG. 3 with further details of the control circuit of the apparatus.

The apparatus 210 comprises a control circuit shown in FIG. 4 that controls the irrigation pump 214 as a function of a predetermined nominal flow rate ($Q_s$), which shall prevail in the body cavity 212. The predetermined nominal flow rate $Q_s$ may be adjusted in a simple manner by setting a certain rotational speed (n) of the irrigation pump 214, for instance, when the irrigation pump 214 is a roller pump.

The control circuit, however, controls the irrigation pump 214 not only as a function of one predetermined nominal flow rate, but as a function of two nominal flow rates $Q_1$ and $Q_2$, a higher and a lower one, to which two respective rotational speeds $n_1$ (higher nominal flow rate) and $n_2$ (lower nominal flow rate) are associated.

In contrast to that, the suction pump 224 is controlled by the control circuit as a function of a predetermined nominal pressure ($p_s$) (i.e. broken line 225 in FIG. 3), which shall prevail in the body cavity 212. The suction pump 224 is further controlled by the control circuit as a function of the actual pressure p acquired by the pressure sensor 228 for maintaining the predetermined nominal pressure $p_s$ in the body cavity 212. The suction pump 224 may be variably controlled at two differing flow rates that may comprise either two differing specific flow rates or two differing ranges, both having a higher nominal flow rate the lower nominal flow rate.

The suction pump 224 is a displacement pump too, which is a roller pump in the present case, but may also be a gear pump.

As already mentioned, the irrigation pump 214 is controlled as a function of at least two predetermined nominal flow rates $Q_1$ and $Q_2$ corresponding to two predetermined rotational speeds $n_1$ and $n_2$ of the irrigation pump 214. The control circuit comprises a control unit 236 for the working instrument 223, which automatically switches over between these both nominal flow rates $Q_1$ and $Q_2$ via e.g. a relay 238 and switches 240 and 242 as a function of the operating condition of the already mentioned working instrument 223 connected with the second suction conduit 222. When the working instrument 223, for example a resection instrument, is actuated, the control circuit automatically adjusts the irrigation pump 214 to the higher nominal flow rate $Q_1$ corresponding to the higher rotational speed $n_1$, and upon switching off the working instrument, the control circuit automatically switches over to the lower nominal flow rate $Q_2$ corresponding to the lower rotational speed $n_2$, or vice versa.

In addition, the control circuit also effects the automatic changeover between the suction of the liquid from the body cavity 212 via the first suction conduit 220 or the second suction conduit 222, when the working instrument 223 is switched on so that the liquid, possibly along with body liquids and tissue pieces, is then drawn off via the second suction conduit 222 through the working instrument 223.

Valves 232 and 234, for example tube squeezing valves, are provided on the first suction conduit 220 and on the second suction conduit 222 schematically shown in FIG. 3 which are controlled by the control circuit, and which may be closed and opened via switches 244 and 246 connected with the control unit 36 for the working instrument 223, in order to change over between the suction conduits 220 and 222.

With reference to FIG. 4, the control circuit further comprises a controller 248, which is connected, at the input side, with a subtractor or comparator 250, which is supplied, at the input side, with the signal of the respectively set nominal flow rate $Q_1$ or $Q_2$, and also with the signal of the actual rotational speed $n_{ist}$ of the suction pump 224, which corresponds to an actual flow rate $Q_{ist}$, in particular when the suction pump 224 is a roller pump as it is in the shown embodiment. The controller 248 is connected, at the output side, with the irrigation pump 214, and feeds a signal corresponding to the nominal flow rate $Q_s$ thereto.

The pressure sensor 228 further feeds a signal to another subtractor or comparator 252, which signal corresponds to the actual pressure p acquired by the pressure sensor 228. The subtractor or comparator 252 is further connected, at the input side, with a nominal pressure value generator (not shown) feeding a signal corresponding to the nominal pressure $p_s$ to the sutractor or comparator 252. The subtractor or comparator 252 is connected, at the output side, with another controller 254, which is connected, at the output side, with the suction pump 224.

In the following, the control of the apparatus 200 is now described in more detail.

The control of the suction pump 224 for maintaining the nominal pressure $p_s$ in the body cavity 212 as a function of the actual pressure p determined by the pressure sensor 228 (broken lines 229 in FIG. 3) is such that the speed of the suction pump 224 is increased when the actual pressure p exceeds the nominal pressure $p_s$, and the speed of the suction pump 224 is reduced accordingly, when the actual pressure p drops under the nominal pressure $p_s$.

In case that the irrigation pump 214 is a gear pump, the flow rate produced by the irrigation pump 214 is not correlated with the speed of the irrigation pump 214 in a single-valued manner, as it usually is the case with a roller pump. For a gear pump, the flow rate depends on the irrigation pressure in the irrigation conduit 216 as well as on the suction pressure in the suction conduit 220 or 222. For this reason, it is not possible to control the flow rate only by means of the speed of the irrigation pump 214, but a regulation is necessary. Therefore, the control circuit is configured such that the rotational speed $n_{ist}$ of the suction pump 224 is fed back to the irrigation pump 214, i.e. the control circuit uses the speed $n_{ist}$ of the suction pump as a control signal for the actual flow rate. When the liquid flows unimpeded through the body cavity 212 and no liquid enters into the blood stream, i.e. when the flow rate in the irrigation conduit 16 and in the suction conduit 220 or 222 are equal, an independent adjustment of the flow rate and of the pressure is possible without difficulty.

Now, when the nominal flow rate increases from e.g. $Q_2$ to $Q_1$ as a function of which the irrigation pump 214 is controlled as already mentioned, the controller 248 will increase the speed n of the irrigation pump 214, whereby the actual pressure p in the irrigation conduit 216 would increase. This would cause the suction pump 224 to increase its speed $n_{ist}$ via the controller 254, in order to reduce the actual pressure p again, and this will be continued as long as the flow rate $Q_1$ in the suction conduit 220 or 222 is adjusted to the newly predetermined flow rate $Q_1$ in the irrigation conduit 216.

On the other hand, if the nominal pressure $p_s$ is increased, the controller 254 would slow down the speed $n_{ist}$ of the suction pump 224 for the time. This would result in a control deviation for the irrigation pump 214, which, for the time, increases its speed n, which results in a further increase of the actual pressures, which further in turn, the suction pump 224 tries to compensate for by an increase of the suction power. In this manner, an increase of the nominal pressure $p_s$ may be obtained without the nominal flow rate $Q_s$ being changed in the end.

When an obstruction, however, occurs in the suction conduit 220 or 222 that would impede the outflow of the liquid from the body cavity 212, another mechanism arises that is caused by the fact that the pressure in the suction conduit 220 or 222 decreases when in general the speed of a roller pump is increased without liquid being able to continue to flow in a sufficient quantity. This results in the pump tube of the roller pump not reaching its complete cross-section in the suction region, i.e. the pump tube partially collapses so that the flow rate does not increase to the same degree or even decreases despite of the increased speed $n_{ist}$ of the suction pump. This in turn effects the irrigation pump 214, according to the speed $n_{ist}$ of the suction pump 224, which is a measure of the actual flow rate $Q_{ist}$ for the irrigation pump 214, must assume that the actual flow rate $Q_{ist}$ is too high and reduces its speed n accordingly. This results in the desired effect that the pressure in the body cavity 212 is again reduced or not further increased by virtue of the more and more decreasing speed n of the irrigation pump 214.

The afore-mentioned control dependency not only works when the irrigation pump 214 is a gear pump, but also in case the irrigation pump 214 is a roller pump.

Furthermore, it is possible to determine the loss of liquid in the body cavity 212 by a subtraction of both speeds $n_{ist}$ of the suction pump 224 and the irrigation pump 214, in particular when the irrigation pump 214 and the suction pump 224 are both roller pumps.

Figure 5:
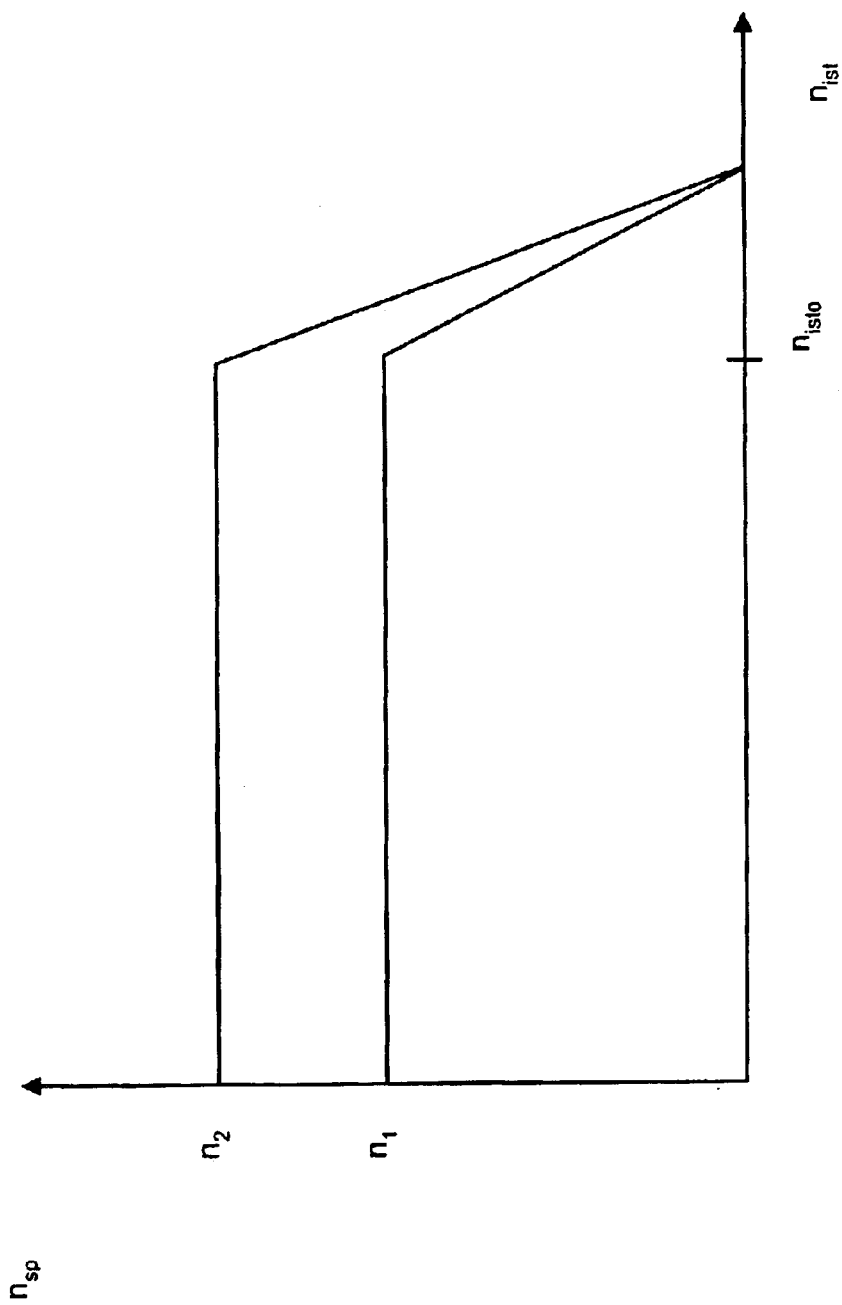
FIG. 5 shows a graph of modified control dependency between the irrigation pump and the suction pump of the apparatus in FIGS. 1 and 3.

A slightly modified control of the irrigation pump 214 as a function of the suction pump 224 is schematically shown in FIG. 5. In case of an obstruction in the first suction conduit 220 or the second suction conduit 222, the actual pressure p in the body cavity 212 increases, because the irrigation pump 214 further feeds irrigation liquid via the irrigation conduit 216 into the body cavity 212. Since the suction pump 224 is controlled as a function of the predetermined nominal pressure $p_s$, the increase of pressure p in the body cavity 212 results in a higher suction power of the suction pump 224 which is manifested in a higher speed $n_{ist}$ of the suction pump 224. In case of lighter obstructions, the increase of the suction power of the suction pump 224 is sufficient to draw off the obstruction, which is caused, for example, by tissue sticking in the suction conduit 220 or suction conduit 222. In case, however, the removal of the obstruction is not possible, the speed $n_{ist}$ of the suction pump 224 will further increase and exceed a predetermined threshold value $n_{ist0}$. By virtue of the feedback of the speed $n_{ist}$ of the suction pump 224 to the irrigation pump 214, exceeding the predetermined threshold value $n_{ist0}$ of the speed $n_{ist}$ of the suction pump 224 will result in a decreasing speed n, if necessary until the irrigation pump 214 is slowed down to zero speed.

Another control dependency of the irrigation pump may consist in a control of the irrigation pump as a function of the difference of the speeds of the suction pump and the irrigation pump.

Figure 6:
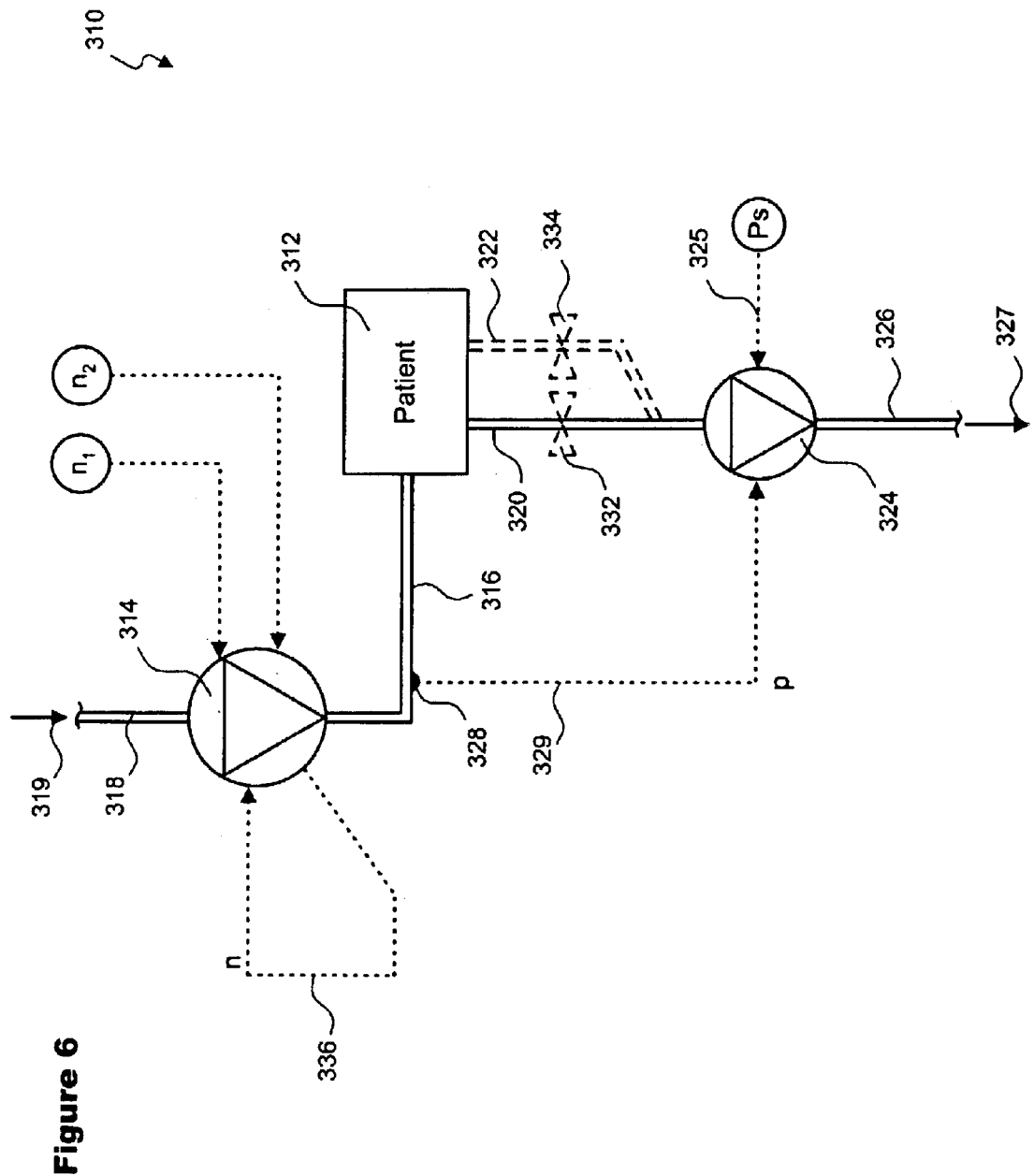
FIG. 6 is a diagram of an apparatus for irrigating a body cavity according to another advantageous embodiment of the present invention.

With reference to FIG. 6, there is shown an apparatus 300 for irrigating a body cavity 312 with a liquid, which differs from the apparatus 300 only in that the irrigation pump 314 is not controlled as a function of the suction power of the suction pump 324. The irrigation pump 314 is rather controlled as a function of the predetermined nominal flow rate or at least two predetermined nominal flow rates corresponding to two predetermined speeds $n_1$ and $n_2$ only so that the predetermined nominal flow rates are maintained in the body cavity 312, as indicated by a broken line 336. Apart from that, the apparatus 300 does not differ from the apparatus 200 so that reference may be made to the description of the apparatus 200.

In the afore-described embodiment, the irrigation pump 214 or the irrigation pump 314 may be designed as a centrifugal pump instead of a gear pump or, in general, a displacement pump. In case that such a centrifugal pump is used as the irrigation pump, the correlation between the flow rate and the speed of the centrifugal pump is first determined, and the control circuit then uses this correlation in order to adjust or maintain the nominal flow rate.

Figure 7:
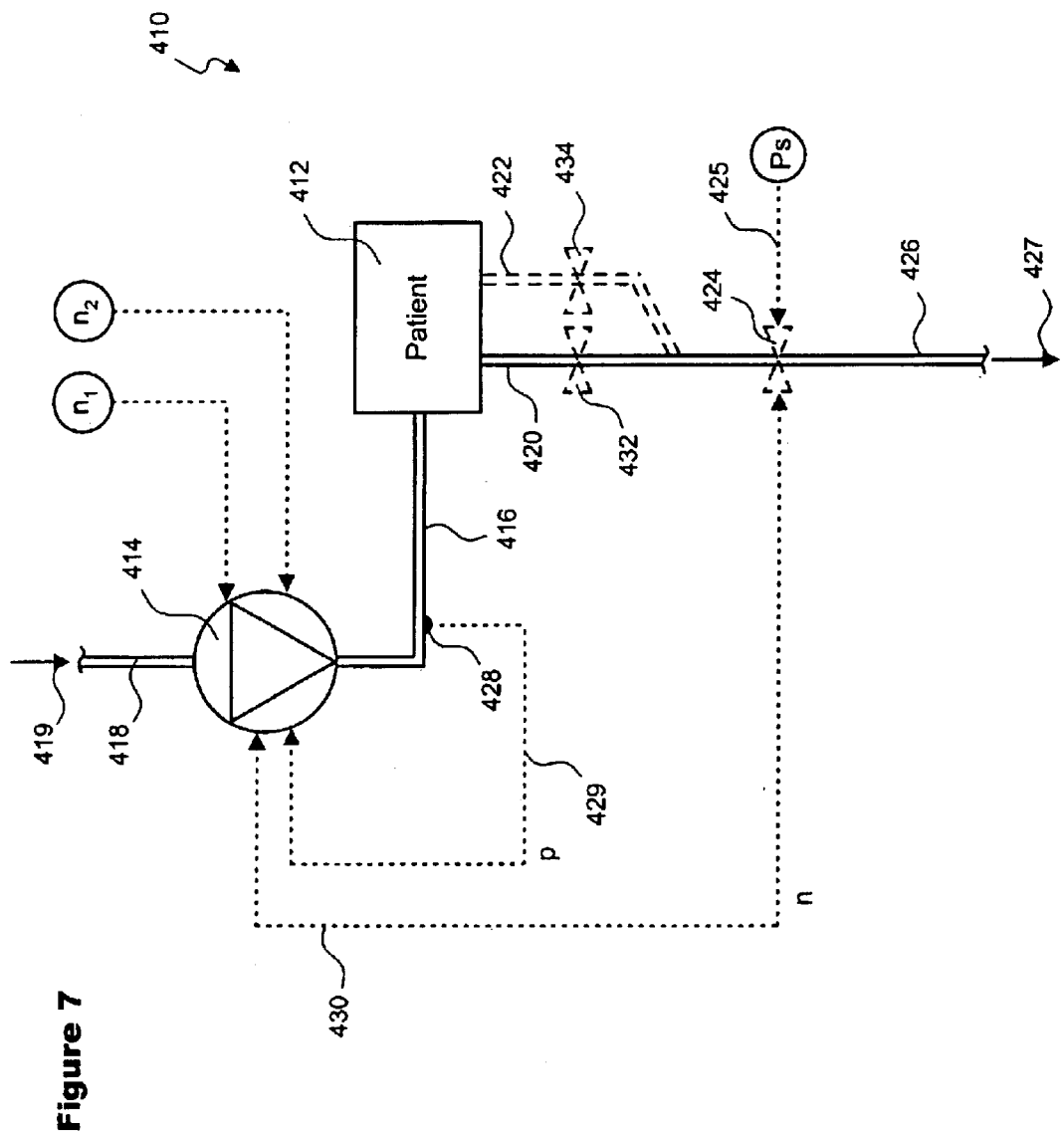
FIG. 7 is a diagram of an apparatus for irrigating a body cavity according to yet another advantageous embodiment of the present invention.

With reference to FIG. 7, there is shown an apparatus 400 for irrigating a body cavity 412 with a liquid. The liquid is drawn from a liquid reservoir (not shown) via a conduit 418 according to an arrow 419. An irrigation pump 414 is controlled as a function of the pressure (p) measured in the irrigation conduit 416. This pressure is measured by means of pressure sensor 428.

A first suction conduit 420 leads from the body cavity 412 to an output valve 424 downstream of the body cavity 412. A second suction conduit 422, also leads from the body cavity 412 to the output valve 424. The first suction conduit 420 is connected with an irrigation instrument not shown in detail, which may be inserted in the body cavity 412. The second suction conduit 422 is connected with a working instrument (not shown), for example a resection instrument, which is used for withdrawing fluid and particles as well as for carrying out an operation in the body cavity 412.

Valves 432 and 434, are provided on the first suction conduit 420 and on the second suction conduit 422, and are controlled by a control circuit, in order to change over between the suction conduits 420 and 422.

The liquid along with body liquids like blood, secretions and tissue pieces is drained from the body cavity 412 by means of either suction conduit 420 or 422 through the output valve 424. The liquid is then drained off via a conduit 426 according to an arrow 427 to a collecting vessel (not shown).

The control circuit controls the irrigation pump 414 as a function of a nominal pressure ($p_s$) (i.e. broken line 429), which shall prevail in the body cavity 412. The irrigation pump 414 is further controlled by actuation of the two valves 432 and 434. When valve 432 is actuated, the irrigation pump 414 is fed a first nominal flow rate ($n_1$), and when valve 434 is actuated, the irrigation pump 414 is fed a second nominal flow rate ($n_2$) that is higher than the first nominal flow rate ($n_1$). The irrigation pump 414 is therefore variably controlled at two differing settings; the higher nominal flow rate ($n_2$) and the lower nominal flow rate ($n_1$).

The output valve 424 is controlled by the nominal flow rate ($Q_s$) (i.e. broken line 430). The output valve 424 is further controlled by the control circuit as a function of the actual pressure p acquired by the pressure sensor 428 for maintaining the nominal pressure $p_s$ in the body cavity 412. The output valve 424 is therefore variably controlled in two differing ranges; the higher nominal flow rate ($n_2$) and the lower nominal flow rate ($n_1$).

Although the invention has been described with reference to a particular arrangement of parts, features and the like, these are not intended to exhaust all possible arrangements or features, and indeed many other modifications and variations will be ascertainable to those of skill in the art.

What is claimed is:

1. An apparatus for irrigating a body cavity with a liquid, comprising:
   an irrigation pump;
   an irrigation conduit, connected to said irrigation pump at a first end and connected to a body cavity at a second end, for feeding the liquid into the body cavity;
   a suction pump;
   a suction conduit, connected to said suction pump at a first end and connected to the body cavity at a second end, for withdrawing the liquid from the body cavity; and
   a control circuit, which controls said irrigation pump and said suction pump such that the liquid passes through the body cavity substantially with a nominal pressure and a nominal flow rate;
      wherein the control circuit controls the irrigation pump as a function of the nominal flow rate through the body cavity, and controls the suction pump as a function of the nominal pressure within the body cavity; and
      wherein said control circuit controls said irrigation pump as a function of the suction power of said suction pump such that the power of said irrigation pump is reduced when the suction power of said suction pump is increased, at least when the suction power of the suction pump exceeds a threshold value.

2. The apparatus of claim 1, further comprising a pressure sensor for determining the actual pressure in the body cavity, wherein said control circuit controls said suction pump as a function of the actual pressure determined by said pressure sensor for maintaining the nominal pressure.

3. The apparatus of claim 1, wherein said irrigation pump or said suction pump are displacement pumps.

4. The apparatus of claim 1, wherein said irrigation pump is selected from the group consisting of: a roller pump or a gear pump.

5. The apparatus of claim 3, wherein said suction pump is a roller pump.

6. The apparatus of claim 1, wherein said irrigation pump is a centrifugal pump.

7. The apparatus of claim 1, wherein said control circuit uses the speed of said suction pump as a control signal and controls said irrigation pump as a function of the control signal.

8. The apparatus of claim 7, wherein said control circuit controls said irrigation pump as a function of the speed of said suction pump, at least when a flow rate threshold value is exceeded, such that the speed of said irrigation pump is reduced when the speed of the suction pump increases.

9. The apparatus of claim 1, wherein said control circuit controls said irrigation pump as a function of the difference between the speeds of said irrigation pump and said suction pump.

10. The apparatus of claim 1, wherein said control circuit controls said irrigation pump as a function of at least two different nominal flow rates ($Q_1$, $Q_2$).

11. The apparatus of claim 10, wherein said control circuit switches over said irrigation pump between the at least two nominal flow rates ($Q_1$, $Q_2$) as a function of the operating condition of a working instrument connected with said control circuit.

12. The apparatus of claim 1, further comprising:
a first suction conduit, connected to the body cavity at a first end and said suction pump at a second end; and
a second suction conduit, connected to a working instrument at a first end, the working instrument being insertable into the body cavity, and said suction pump at a second end;
wherein the working instrument may be switched over between both suction conduits as a function of the operating condition of the working instrument.

13. The apparatus of claim 1, wherein said control circuit determines the difference between the speeds of said suction pump and said irrigation pump.

14. An apparatus for irrigating a body cavity with a liquid, comprising:
an irrigation pump;
an irrigation conduit, connected to said irrigation pump at a first end and connected to a body cavity at a second end, for feeding the liquid into the body cavity;
a working tool, insertable into the body cavity;
a suction pump;
a first suction conduit, connected to the body cavity at a first end and connected to said suction pump at a second end, for withdrawing the liquid from the body cavity at a first range of variable flow rates;
a second suction conduit, connected to said working tool at a first end and connected to said suction pump at a second end, for withdrawing the liquid from the body cavity at a second range of variable flow rates, the second range of variable flow rates being higher than the first range of variable flow rates; and
a control circuit, which controls said irrigation pump and said suction pump such that the liquid passes through the body cavity substantially with a predetermined nominal pressure and a predetermined nominal flow rate.

15. The apparatus of claim 14, wherein said control circuit controls the irrigation pump as a function of the nominal flow rate, and controls the suction pump as a function of the nominal pressure.

16. The apparatus of claim 14, wherein said control circuit controls said irrigation pump as a function of the suction power of said suction pump such that the power of said irrigation pump is reduced when the suction power of said suction pump is increased, at least when the suction power of the suction pump exceeds a predetermined threshold value.

17. The apparatus of claim 14, wherein said control circuit uses the speed of said suction pump as a control signal and controls said irrigation pump as a function of the control signal.

18. The apparatus of claim 17, wherein said control circuit controls said irrigation pump as a function of the speed of said suction pump, at least when a flow rate threshold value is exceeded, such that the speed of said irrigation pump is reduced when the speed of the suction pump increases.

19. A method for irrigating a body cavity with a liquid, comprising the steps of:
providing an irrigation pump;
connecting an irrigation conduit between the irrigation pump and a body cavity, for feeding the liquid into the body cavity;
providing a suction pump;
connecting a suction conduit between the body cavity and the suction pump, for withdrawing the liquid from the body cavity;
providing a control circuit, which controls said irrigation pump and said suction pump such that the liquid passes through the body cavity substantially with a nominal pressure and a nominal flow rate;
controlling the irrigation pump as a function of the nominal flow rate through the body cavity;
controlling the suction pump as a function of the nominal pressure through the body cavity; and
controlling the irrigation pump as a function of the suction power of said suction pump such that the power of said irrigation pump is reduced when the suction power of said suction pump is increased, at least when the suction power of the suction pump exceeds a threshold value.

20. A method for irrigating a body cavity with a liquid, comprising the steps of:
providing an irrigation pump;
connecting an irrigation conduit, between the irrigation pump and a body cavity, for feeding the liquid into the body cavity;
providing a working tool that is insertable into the body cavity;
providing a suction pump;
connecting a first suction conduit between the body cavity and the suction pump, for withdrawing the liquid from the body cavity at a first range of variable flow rates;
connecting a second suction conduit between the working tool and the suction pump, for withdrawing the liquid from the body cavity at a second range of variable flow rates, the second range of variable flow rates being higher than the first range of variable flow rates
providing a control circuit, which controls said irrigation pump and said suction pump such that the liquid passes through the body cavity substantially with a nominal pressure and a nominal flow rate;
withdrawing the liquid from the body cavity at a first range of variable flow rates through the first suction conduit when the working tool is not activated; and
withdrawing the liquid from the body cavity at a second range of variable flow rates through the second suction conduit when the working tool is activated.

21. An apparatus for irrigating a body cavity with a liquid, comprising:
an irrigation pump;
an irrigation conduit, connected to said irrigation pump at a first end and connected to a body cavity at a second end, for feeding the liquid into the body cavity;
an output valve;
a output conduit, connected to said output valve at a first end and connected to the body cavity at a second end, for withdrawing the liquid from the body cavity; and
a control circuit, which controls said irrigation pump and said output valve such that the liquid passes through the body cavity substantially with a nominal pressure and a nominal flow rate;
wherein the control circuit controls the irrigation pump as a function of the nominal pressure within the body cavity, and controls the output valve as a function of the nominal flow rate through the body cavity; and
wherein said control circuit controls said irrigation pump as a function of the suction power of said suction pump such that the power of said irrigation pump is reduced when the suction power of said suction pump is increased, at least when the suction power of the suction pump exceeds a threshold value.

22. An apparatus for irrigating a body with a liquid, comprising:
- an irrigation pump, connected to the body cavity by an irrigation conduit, for irrigating the body cavity with the liquid;
- a suction pump, connected to the body cavity by an output conduit, for withdrawing the liquid from the body cavity; and
  - wherein said irrigation pump is controlled according to a measured flow of liquid in the irrigation conduit and said suction pump is controlled according to a measured pressure in the body cavity; and
  - wherein said irrigation pump is controlled as a function of the measured flow of liquid through the irrigation conduit and the speed of said suction pump such that the speed of said irrigation pump is decreased when the speed of said suction pump exceeds a threshold value.

23. The apparatus of claim 22, further comprising a pressure transducer for determining the actual pressure in the body cavity, wherein said suction pump is further controlled as a function of the actual pressure determined by said pressure transducer for maintaining the nominal pressure.

24. The apparatus of claim 22, wherein said irrigation pump or said suction pump are displacement pumps.

25. The apparatus of claim 22, wherein said irrigation pump is selected from the group consisting of: a roller pump or a gear pump.

26. The apparatus of claim 24, wherein said suction pump is a roller pump.

27. The apparatus of claim 22, wherein said irrigation pump is a centrifugal pump.

28. An apparatus for irrigating a body cavity with a liquid, comprising:
- an irrigation pump, connected to the body cavity by an irrigation conduit, for irrigating the body cavity with the liquid;
- a suction pump, connected to the body cavity by an output conduit, for withdrawing the liquid from the body cavity; and
  - wherein said irrigation pump is controlled according to a measured flow of liquid in the irrigation conduit and said suction pump is controlled according to a measured pressure in the body cavity; and
  - wherein a measured speed of said suction pump is utilized to control said irrigation pump.

29. The apparatus of claim 28, wherein said irrigation pump is controlled as a function of the speed of said suction pump, when a speed threshold value is exceeded by the suction pump, such that the speed of said irrigation pump is reduced when the speed of the suction pump increases.

30. An apparatus for irrigating a body cavity with a liquid, comprising:
- an irrigation pump, connected to the body cavity by an irrigation conduit, for irrigating the body cavity with the liquid;
- a suction pump, connected to the body cavity by an output conduit, for withdrawing the liquid from the body cavity; and
  - wherein said irrigation pump is controlled according to a measured flow of liquid in the irrigation conduit and said suction pump is controlled according to a measured pressure in the body cavity; and
  - wherein said irrigation pump is controlled as a function of the difference between speeds of said irrigation pump and said suction pump.

31. An apparatus for irrigating a body cavity with a liquid, comprising:
- an irrigation pump, connected to the body cavity by an irrigation conduit, for irrigating the body cavity with the liquid;
- a suction pump, connectd to the body cavity by an output conduit, for withdrawing the liquid from the body cavity; and
  - wherein said irrigation pump is controlled according to a measured flow of liquid in the irrigation conduit and said suction pump is controlled according to a measured pressure in the body cavity; and
  - wherein said irrigation pump is controlled as a function of at least two different nominal flow rates.

32. The apparatus of claim 31, wherein said at least two different nominal flow rates comprises two differing flow ranges.

33. The apparatus of claim 31, wherein said irrigation pump is switched between the at least two nominal flow rates as a function of an operating condition of a working instrument.

34. The apparatus of claim 33, further comprising:
- a first suction conduit, connected to the body cavity at a first end and said suction pump at a second end; and
- a second suction conduit, connected to a working instrument at a first end, the working instrument being insertable into the body cavity, and said suction pump at a second end;
  - wherein the working instrument may be switched between said suction conduits alternately as a function of the operating condition of the working instrument.

* * * * *